US00PP21067P2

(12) United States Plant Patent

Klemm et al.

(10) Patent No.: US PP21,067 P2

(45) Date of Patent: Jun. 15, 2010

(54) *PELARGONIUM* PLANT NAMED 'KLEPZ08220'

(50) Latin Name: *Pelargonium zonale*
Varietal Denomination: KLEPZ08220

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,394

(22) Filed: Mar. 24, 2009

(51) Int. Cl.
*A01H 5/00* (2006.01)

(52) U.S. Cl. ..... Plt./327

(58) Field of Classification Search ..... Plt./327
See application file for complete search history.

*Primary Examiner*—Susan B McCormick Ewoldt
(74) *Attorney, Agent, or Firm*—Jondle & Associates, P.C.

(57) ABSTRACT

A new cultivar of *Pelargonium* named 'KLEPZ08220' particularly characterized with orange, shiny inflorescences, medium growth, good performance indoors and outdoors, and early and rich flowering habit, is disclosed.

1 Drawing Sheet

Genus and Species: *Pelargonium zonale.*
Variety denomination: 'KLEPZ08220'.

BACKGROUND OF THE NEW PLANT

The present invention comprises a new and distinct cultivar of *Pelargonium*, botanically known as *Pelargonium zonale*, and hereinafter referred to by the cultivar name 'KLEPZ08220'. 'KLEPZ08220' was discovered as a seedling resulting from a cross in September 2001 in Stuttgart, Germany between the proprietary female *Pelargonium* parent, 'Z 99 289' (unpatented) and the proprietary male *Pelargonium* parent, 'Kleugudo' (U.S. Plant Pat. No. 8,886). A single plant selection was subsequently chosen for further evaluation and for asexual propagation.

The new cultivar was created in 2001 and first propagated in October 2001 in Stuttgart, Germany and has been asexually reproduced repeatedly by vegetative cuttings in Stuttgart, Germany over an eight-year period. 'KLEPZ08220' has been found to retain its distinctive characteristics through successive asexual propagations.

Plant Breeder's Rights for this cultivar were applied for in Switzerland on Jun. 19, 2008 and in Canada on Mar. 28, 2008. 'KLEPZ08220' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Orange, shiny inflorescences;
2. Medium growth;
3. Good performance indoors and outdoors; and
4. Early and rich flowering habit.

DESCRIPTION OF THE PHOTOGRAPH

This new *Pelargonium* plant is illustrated by the accompanying photograph which shows blooms, buds, and foliage of the plant; the colors shown are as true as can be reasonably obtained by conventional photographic procedures. The photograph is of a plant about 3-months old taken in Spring 2008 and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPZ08220'. The data which define these characteristics were collected from asexual reproductions carried out in Stuttgart, Germany. The plant history was taken on 3-month old, un-pinched plants in 12-cm pots in a greenhouse in January through April. The color readings were determined under natural light. Color references are to the RHS Colour Chart of The Royal Horticultural Society of London (R.H.S.) (2001).

DETAILED BOTANICAL DESCRIPTION

Classification:
- *Family.*—Geraniacaea.
- *Species.*—*Pelargonium zonale.*
- *Common name.*—*Pelargonium* (Geranium).
- *Denomination.*—'KLEPZ08220'.

Parentage:
- *Female parent.*—The proprietary female *Pelargonium* parent, 'Z 99 289' (unpatented).
- *Male parent.*—The proprietary male *Pelargonium* parent, 'Kleugudo' (U.S. Plant Pat. No. 8,886).

Plant:
- *Habit.*—Upright.
- *Height.*—16.0 cm.
- *Spread.*—25.0 cm.
- *Life cycle.*—Spring to autumn.
- *Form.*—Round, bushy.
- *Time to produce a rooted cutting.*—17 days.
- *Time to bloom from propagation.*—Approximately 75 days.
- *Lastingness of inflorescence on the plant.*—12 to 15 days.

Stems:
*Stem color.*—RHS 137C.
*Pubescence.*—Weak, short hairs.
*Pubescence color.*—Greenish white.
*Stem form.*—Round.
*Diameter.*—0.8 cm to 1.0 cm.
*Length.*—8.0 cm to 10.0 cm.
*Internode length.*—About 0.8 cm to 2.0 cm.
Leaves:
*Arrangement.*—Alternate.
*Shape.*—Round.
*Apex.*—Round.
*Base.*—Open.
*Margin.*—Entire.
*Surface appearance* (*both surfaces*).—Dull.
*Length.*—4.0 cm to 6.0 cm.
*Width.*—4.0 cm to 7.0 cm.
*Color.*—Upper surface: RHS 137A. Lower surface: RHS 137C.
*Surface texture* (*both surfaces*).—Pubescent.
*Petiole.*—Length: 2.0 cm to 7.0 cm.
*Color.*—RHS 137C.
*Venation pattern.*—Palmate.
*Venation color.*—RHS 137C.
Inflorescence:
*Flowering habit.*—Continuous.
*Umbels.*—Height: 6.0 cm to 8.0 cm. Diameter: 9.0 to 11.0 cm.
*Individual florets of the umbel.*—Depth: 1.5 cm. Diameter: 4.0 cm to 5.0 cm.
*Fragrance.*—Absent.
Flower buds:
*Cluster shape.*—Round-ovate.
*Length.*—1.0 cm to 3.0 cm.
*Width.*—1.0 cm to 4.0 cm.
*Texture.*—Smooth (not pubescent).
*Bud.*—Shape: Elliptic, shell-shaped. Apex: Acute. Base: Blunt. Margin: Entire, smooth. Color: RHS 137B. Size: Length: 0.8 cm to 1.0 cm. Width: 0.5 cm to 0.8 cm.
Petals:
*Quantity per flower.*—6 to 9.
*Shape.*—Drop-shaped.
*Apex.*—Round.
*Base.*—Obtuse.
*Margin.*—Entire. Length: 2.6 cm. Width: 1.5 cm.
*Color of lobes.*—Upper lobes (both surfaces): RHS 40B. Lower lobes (both surfaces): RHS 41C.
*Fragrance.*—Absent.
Sepals:
*Number per flower.*—5.
*Shape.*—Lanceolate.
*Apex.*—Acute.
*Base.*—Obtuse.
*Margin.*—Entire.
*Color* (*both surfaces*).—RHS 137B and RHS 178C at the base.
*Length.*—1.0 cm.
*Width.*—0.3 cm to 0.4 cm.
Pedicel:
*Length.*—2.5 cm to 3.8 cm.
*Diameter.*—0.15 cm.
*Color.*—RHS 176C.
Peduncle:
*Length.*—14.0 cm to 18.0 cm.
*Diameter.*—0.4 cm.
*Color.*—RHS 176A and RHS 137C.
*Surface texture.*—Smooth (not pubescent).
Reproductive Organs:
*Stamens.*—Anther length: 0.2 cm. Filament length: 0.5 cm to 0.7 cm. Filament color: RHS 45D and RHS 39C. Pollen amount: Moderate. Pollen color: RHS 32A.
*Pistils.*—Number: 1. Stigma color: RHS 39A. Style length: Small. Style color: RHS 137D. Ovary arrangement: Central, middle.
Fruit/seed set: None observed.
Disease and insect resistance: No particular disease or insect resistance noted.

COMPARISON WITH PARENTAL AND COMMERCIAL CULTIVARS

'KLEPZ08220' differs from the female parent, the proprietary female *Pelargonium* parent, 'Z 99 289' (unpatented) in that 'KLEPZ08220' has a medium growth habit and a dark-green leaf color, while 'Z 99 289' has a strong growth habit and a light-green leaf color.

'KLEPZ08220' differs from the male parent, the proprietary male *Pelargonium* parent, 'Kleugudo' (U.S. Plant Pat. No. 8,886) in that 'KLEPZ08220' has orange inflorescences and good branching, while 'Kleugudo' (U.S. Plant Pat. No. 8,886) has salmon-orange inflorescences and less branching.

'KLEPZ08220' differs from the commercial comparison variety 'FISTAROL' (U.S. Plant Pat. No. 19,075) in that 'KLEPZ08220' has an entire leaf margin, an open leaf base, a long stem length (8.0 cm to 10.0 cm), and drop-shaped petals, while 'FISTAROL' (U.S. Plant Pat. No. 19,075) has a bi-crenate and somewhat wavy leaf margin, a cordate leaf base, a short stem length (6.0 cm to 8.0 cm), and obovate-shaped petals.

I claim:

1. A new and distinct cultivar of *Pelargonium* plant named 'KLEPZ08220' as shown and described herein.

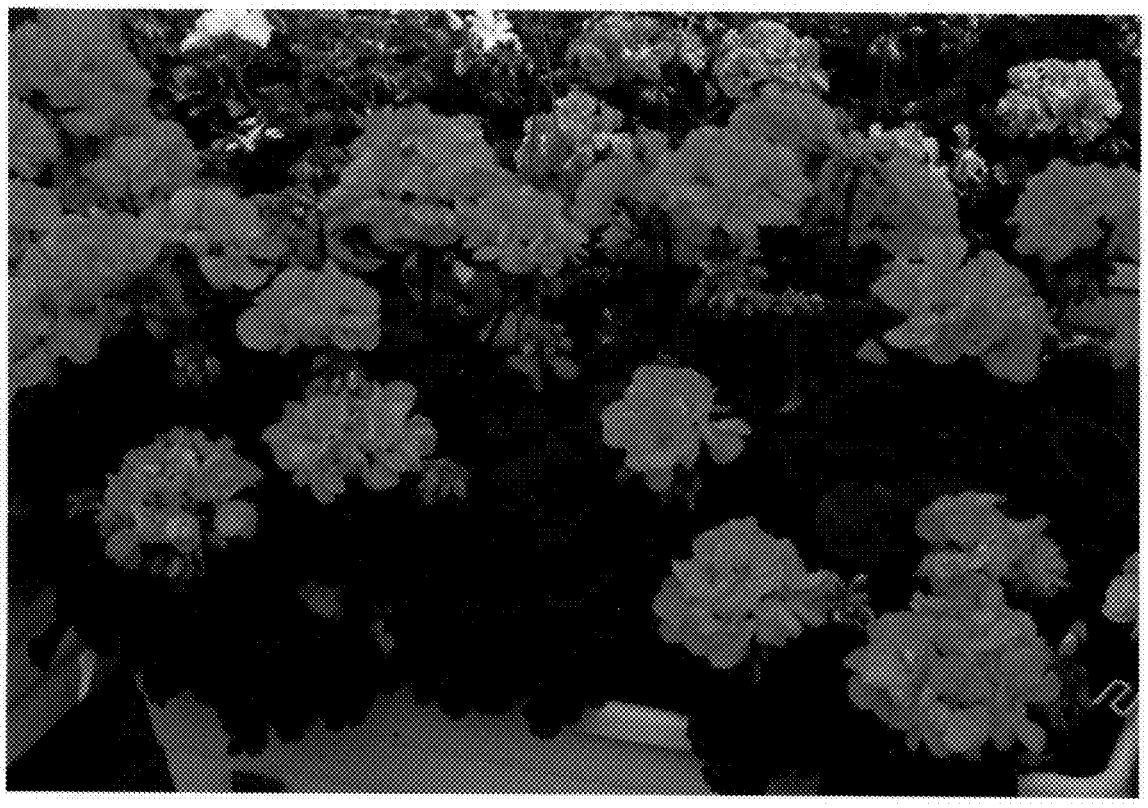

* * * * *